United States Patent [19]
Yost et al.

[11] Patent Number: 5,214,955
[45] Date of Patent: Jun. 1, 1993

[54] CONSTANT FREQUENCY PULSED PHASE-LOCKED LOOP MEASURING DEVICE

[75] Inventors: William T. Yost, Newport News; Peter W. Kushnick, Williamsburg; John H. Cantrell, Tabb, all of Va.

[73] Assignee: The United States of America as represented by the United States National Aeronautics and Space Administration, Washington, D.C.

[21] Appl. No.: 749,737

[22] Filed: Aug. 26, 1991

[51] Int. Cl.[5] .................. G01N 29/18; G01N 9/24
[52] U.S. Cl. ...................... 73/24.05; 374/119; 73/5.97; 73/32 A; 73/61.75; 73/61.79; 73/64.53
[58] Field of Search ............... 73/64.53, 61.79, 61.49, 73/61.75, 597, 602, 703, 24.05, 32 A; 374/119

[56] References Cited
U.S. PATENT DOCUMENTS

| | | | |
|---|---|---|---|
| 3,614,226 | 10/1971 | Vergoz | 356/5 |
| 3,802,271 | 4/1974 | Bertelson | 73/61.75 |
| 4,114,455 | 9/1978 | Walker | 73/597 |
| 4,185,498 | 1/1980 | Watson et al. | 73/597 |
| 4,244,226 | 1/1981 | Green et al. | 73/703 |
| 4,363,242 | 12/1982 | Heyman | 73/579 |
| 4,497,208 | 2/1985 | Oja et al. | 73/61.75 |
| 4,546,641 | 10/1985 | Nguyen | 73/32 A |
| 4,624,142 | 11/1986 | Heyman | 73/597 |

*Primary Examiner*—Hezron E. Williams
*Assistant Examiner*—Rose M. Finley
*Attorney, Agent, or Firm*—Kevin B. Osborne

[57] ABSTRACT

A measuring apparatus uses a fixed frequency oscillator to measure small changes in the phase velocity ultrasonic sound when a sample is exposed to environmental changes such as changes in pressure, temperature, etc. The invention automatically balances electrical phase shifts against the acoustical phase shifts in order to obtain an accurate measurement of electrical phase shifts.

7 Claims, 6 Drawing Sheets

CONSTANT FREQUENCY PULSED PHASE-LOCKED LOOP MEASURING DEVICE

ORIGIN OF THE INVENTION

The invention described herein was jointly made in the performance of work under a NASA contract and by employees of the United States Government and is subject to the provisions of Section 305 of the National Aeronautics and Space Act of 1958, as amended, Public Law 85-568 (72 Stat. 435; 42 U.S.C. 2457).

BACKGROUND OF THE INVENTION

1. Field of the Invention

This invention relates generally to measuring and testing, and more specifically, to a constant frequency pulsed phase-locked loop measuring apparatus.

2. Description of the Related Art

A need exists to characterize states of metals and other materials and systems, for example, by measuring pressure derivatives of ultrasound phase velocities to determine combinations of third-order elastic constants, or by measuring stress derivatives in materials, or other quantities which undergo changes in ultrasonic phase velocities as a function of some thermodynamic variable or variables.

The pulsed superposition technique and the pulse echo overlap technique are generally known and used. Both measure true phase velocity by accurately measuring the time interval necessary for a tone burst to travel round-trip in the sample being measured.

Another system, known as the Blume technique, measures changes in frequency to maintain a "quadrature" condition as some thermodynamic variable changes, and is somewhat similar to a pulsed phase-locked loop. Two examples of a pulsed phase-locked loop are described in U.S. Pat. Nos. 4,363,242 and 4,624,142, both issued to Heyman and assigned to the National Aeronautics and Space Administration (NASA).

In U.S. Pat. No. 4,363,242, the radio frequency output of a voltage controlled oscillator (VCO) is periodically gated to a transducer which produces acoustic waves in a bolt. The reflected acoustic waves are converted to electrical signals by the transducer and gated to a mixer. The mixer also receives the output from the VCO and produces an output which is filtered by a low pass filter. The output of the low pass filter is a DC signal proportional to the phase difference change from a fixed phase difference between the two input signals to the mixer. The DC signal is then sampled at an instance and held by a circuit in response to a "P" signal (from a sample hold). The output of the circuit is integrated and then applied to the VCO to change the frequency of the VCO such that the phase difference between the two inputs to the mixer remains at the fixed phased difference. The frequency of the VCO is thus a measure of the change in strain of the bolt.

In U.S. Pat. No. 4,624,142, a double reference pulse phase locked loop measures the phase shift between the burst signals initially derived from the same periodic signal source, which is also a VCO, and delayed by different amounts because of two different paths. A first path is from a transducer to a front surface of the sample and back, and a second path is from the transducer to the rear surface of the sample and back. A first pulse phase locked loop including a phase detector and phase shifter forces the tone burst signals delayed by the second path in phase quadrature with the periodic signal source. A second pulse phase locked loop including another phase detector forces the tone burst signals delayed by the first path into phase quadrature with the phase shifted periodic signal source.

Some of the problems associated with the known techniques which measure phase velocity, such as the pulse-echo overlap method, is that it cannot be automated easily. Also, the pulse-superposition can cause high amplitudes of drive signal in order to obtain a measurement. In the pulseecho overlap method, it is necessary for an operator to estimate the overlap condition, while in the pulse-superposition method, the superposed pulses must be estimated by amplitude variation, and amplitude variations are not as sensitive to small changes as is phase comparison.

The Blume technique and the pulsed-phase-lock loop use phase comparison techniques, but change phase by changing frequency in order to obtain quadrature between the acoustic signal and the drive signal. This leads to a problem in that the consequences of changing frequency prevents one from measuring changes in true phase velocity and makes the measurement also sensitive to changes in transducer and bond characteristics. Moreover, the frequency change also makes non-contacting capacitive drive techniques incompatible with their operation.

SUMMARY OF THE INVENTION

An object of the present invention is to provide an instrument having sensitivity to small changes in phase velocities.

Another object of the present invention is to provide an instrument which can be easily automated.

These and other objects of the invention are met by providing an apparatus for measuring phase shifts in a sample including a logic and timing circuit, a buffer amplifier-phase shift circuit controlled by voltage, a tone burst formation gate, a fixed frequency oscillator coupled to and sending a constant frequency output to the logic and timing circuit as a clock signal, the buffer amplifier-phase shift circuit as a reference signal, and the tone burst formation gate, a transducer coupled to the tone burst formation gate and being acoustically coupled to the sample, the logic and timing circuit operating the tone burst gate to send an electrical tone burst to the transducer which generates an echo in the sample, the echo being an electrical signal in accordance with the echo, a mixer receiving and comparing phase of the echo generated electrical signal and the reference signal, and outputting an error signal voltage when the phase of the echo generated electrical signal and the reference signal are not in quadrature, and a sample and hold circuit receiving the error signal voltage and passing the error signal voltage to the phase shift circuit through an integrator circuit, thereby adjusting the phase of the reference signal to match the phase of the echo signal, wherein a change in an acoustic parameter of the sample results in a change in the quadrature condition by an alteration in the error signal voltage supplied to the phase-shift circuit, and wherein the alteration in voltage is quantified and calibrated to indicate a condition of the sample.

These and other features and advantages of the measuring apparatus of the present invention will become more apparent with reference to the following detailed description and drawings.

DETAILED DESCRIPTION OF THE PREFERRED EMBODIMENTS

Figure 1:
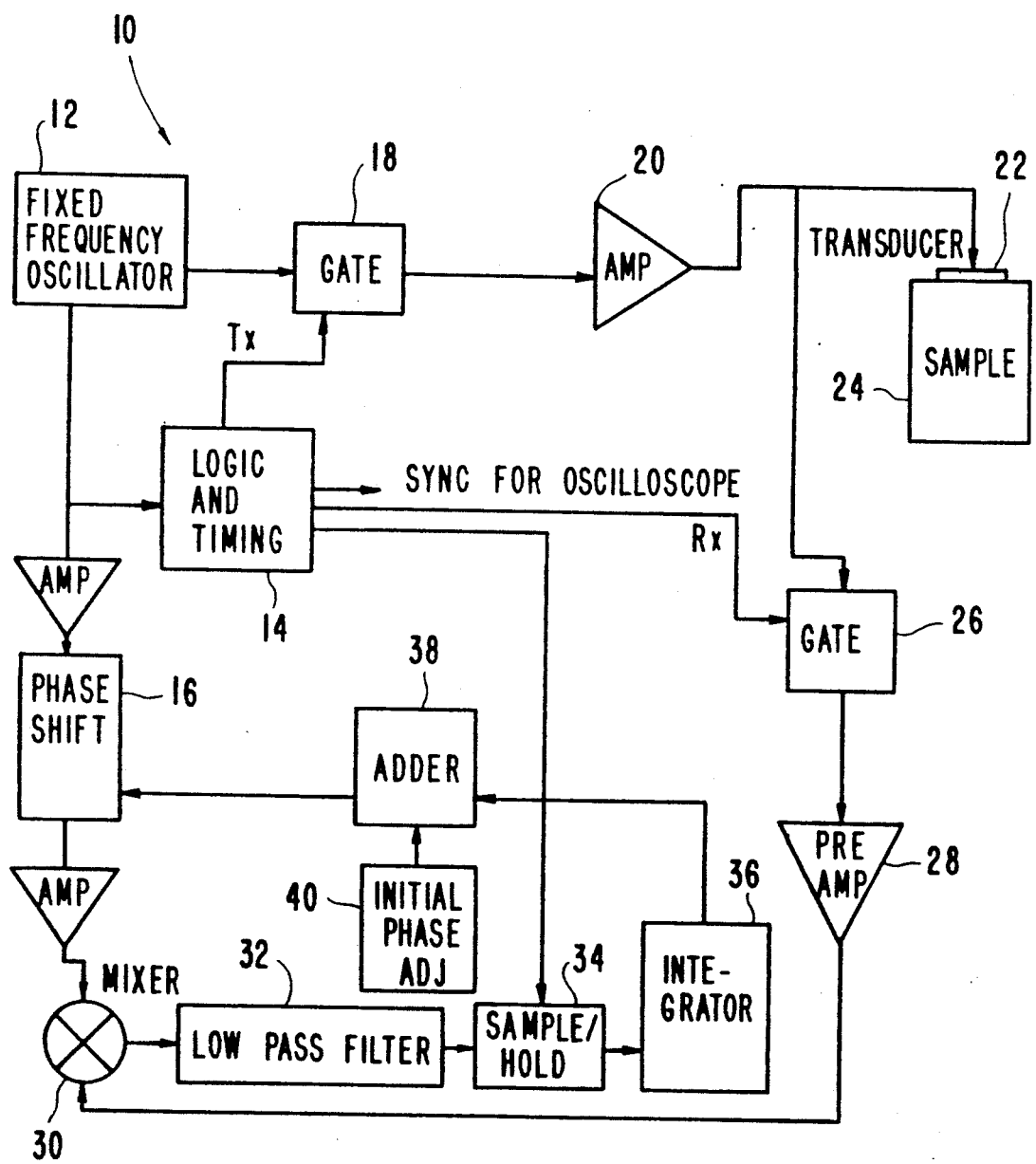
FIG. 1 is a block diagram of a first preferred embodiment of the present invention.

Referring now to FIG. 1, a constant frequency pulsed phase-locked loop is generally referred to by the numeral 10, and includes a fixed frequency oscillator 12, such as a phase-stable synthesizer. The fixed frequency oscillator 12 sends its constant frequency output to three different blocks: the logic and timing circuit 14, a buffer amplifier-phase shift circuit 16, and a tone-burst formation gate 18. The logic and timing circuit 14 uses this signal as a clock and counts down to determine the timing on its outputs. One output is Tx gate to form the electrical tone burst. The logic and timing circuit 14 also contains a setting so that the operator can set the gate for as many cycles as is desired.

The electrical tone burst is amplified by amplifier 20 and delivered to a transducer 22. The transducer 22 responds to the electrical tone-burst by launching an acoustical tone burst in the sample 24. The acoustical tone burst travels down the sample 24 and is reflected from the opposite end and thus travels back through the sample, where it is again reflected by the transducer. This process continues back and forth until the acoustic energy has dissipated, or is otherwise rendered unusable because of phase cancellation, etc. Each acoustic signal round trip, referred to as an "echo", expends some of its energy in transducer excitation, which causes an electrical "echo" from each passage. It is important to note at this time that one could connect another transducer to the opposite end of the sample 24 and connect the receive gate 26 to this second (not shown) transducer. This arrangement involving two transducers is called the "pitch-catch" mode.

A desired echo is selected by adjustments to the logic and timing circuit, which causes the received signal to be passed to a preamplifier 28 through gate 26 by means of Rx gate signal. The signal then proceeds to a mixer 30 where the received signal is phase-compared to the reference signal provided from the fixed frequency oscillator. Unless these two signals are at quadrature, a voltage level, which constitutes an error signal, is generated by the mixer 30 and passed through a low-pass filter 32 to a sample and hold, which is activated by the logic and timing circuit 14. The sample and hold 34 holds the level of voltage until the next pulse-echo cycle (P-Ec). Thus, the sample and hold output is updated at each P-Ec. This output voltage is fed to an integrator circuit 36 whose voltage output is delivered to the phase shift circuit 16 after passing through an adder circuit 38. The adder circuit 38 also receives a voltage adjustment from an initial phase adjustment 40, which may be manually operated by turning a dial. During initial set up the operator thus changes the voltage output of the mixer 30 by using the phase adjustor and adder circuit until the sample and hold voltage output is zero, which occurs at quadrature of the echo and the signal from the main frequency oscillator.

Figure 2:
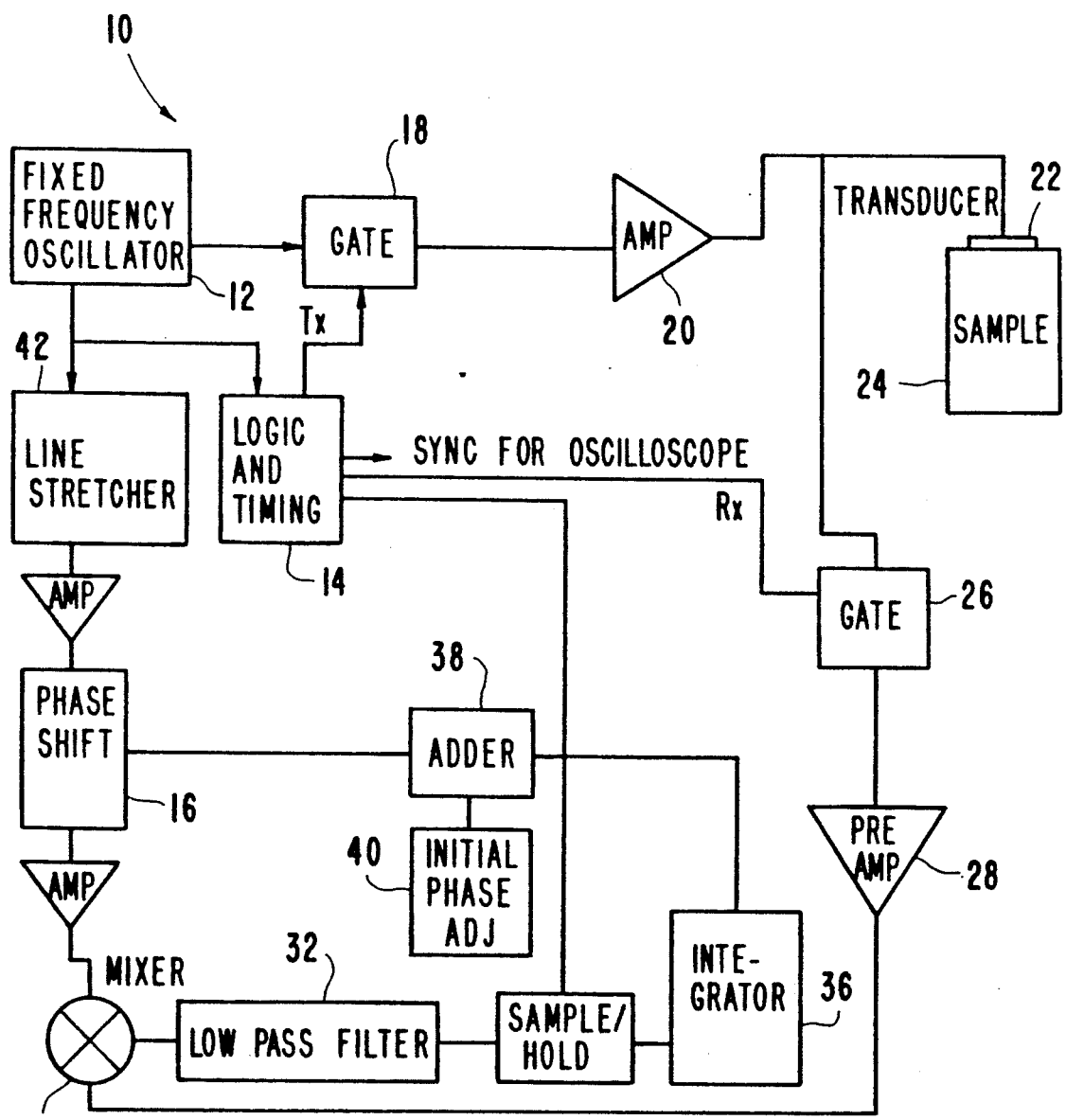
FIG. 2 is a block diagram, showing a variation of the FIG. 1 embodiment.

Any change in the acoustic parameters in the sample can result in a change in the quadrature condition by an alteration in the voltage to the phase shift circuit. One way to quantify a phase change in the sample is to observe the voltage applied to the phase shifter 16. There are a variety of ways in which to quantify the phase shift, however. In order to measure changes in velocity, the results must be measured in terms of the phase shift caused by changes in the traversal of the acoustical signal in the sample. This is affected by change in phase in either the electrical or acoustical parameters. One can use this fact to calibrate by either calibrating the phase shift circuit against input voltage and reading the input voltage changes, or inserting a known, adjustable phase shifter, such as a calibrated line stretcher 42, as shown in FIG. 2, and adjusting until the same input voltage to the phase shifter is obtained. Alternatively, calibration may be achieved by adjusting for quadrature with the line stretcher, then changing the acousting parameter in the sample and readjusting the line stretcher for quadrature to compare the difference.

For absolute velocity calibration, there are numerous alternatives. First, one could set the phase shift circuit input voltage to zero volts. Using cable lines or other such means for adjusting shifts, it is possible to make sure that the two line paths, one from the oscillator to the mixer and the other from the oscillator to sample to gate to preamp to mixer have the same amount of phase shift in the two paths. Then, by counting from the oscillator, each count is equivalent to a phase shift of $2\pi$ radian in the acoustic system. The total phase is then calculated by $\phi = 2\pi$ (count) $+ \pi/2$ or $\phi = 2\pi$ (count) $+ 3\pi/2$, depending on quadrature state.

Figure 3:
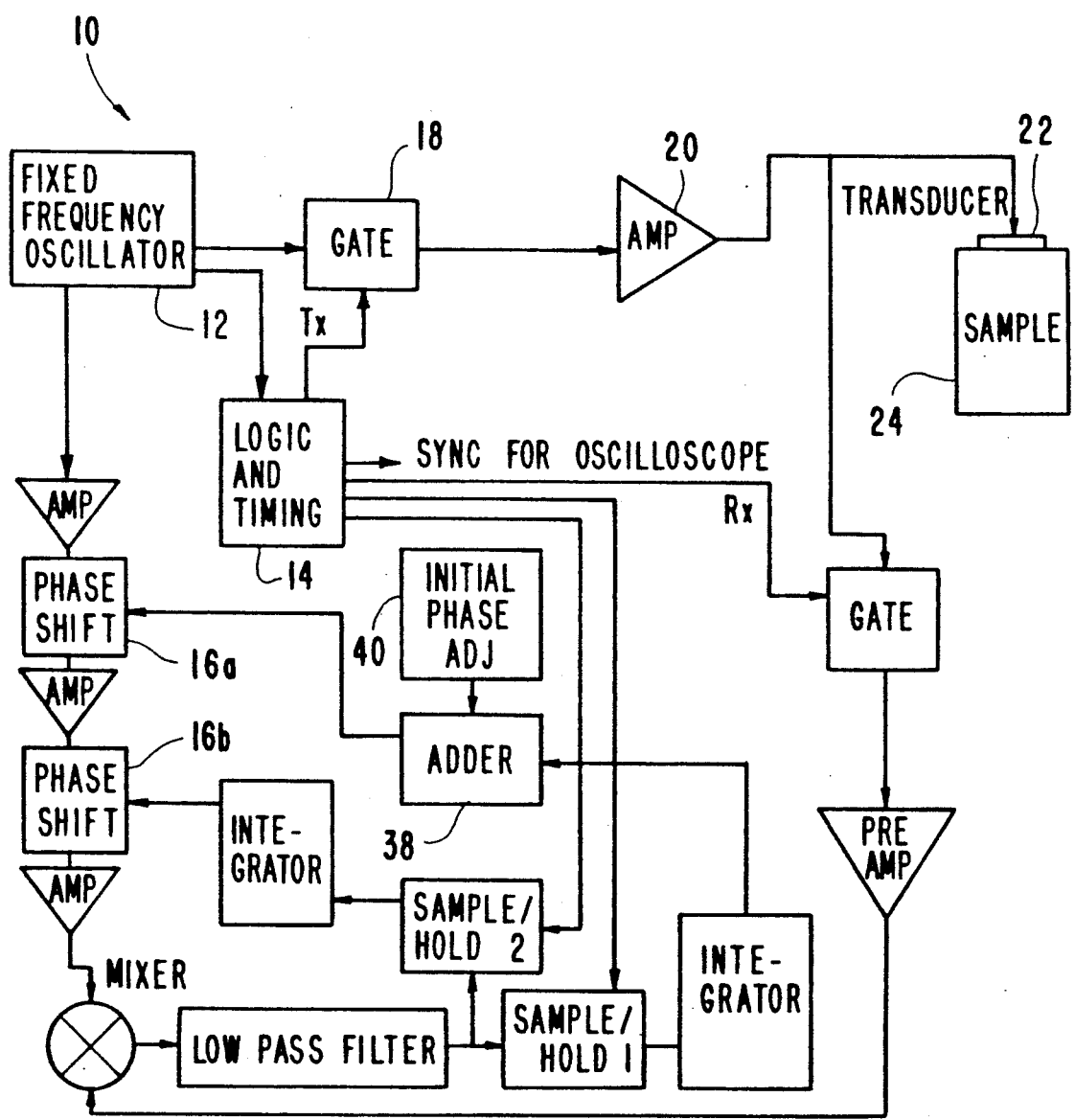
FIG. 3 is a block diagram of a second, preferred embodiment of the present invention.

An alternative embodiment of the invention is illustrated in FIG. 3, where substantial portions of the circuit are repeated. In the FIG. 3 embodiment, however, the initial phase is set by a first phase shifter 16a, and the measurement is made by a second, separate phase shifter 16b. The first phase shifter 16a is provided to give a reference, and the second phase shifter 16b measures the shift between the first signal and the other signal of interest. For example, the first signal can be the first return echo and the second can be one of the other echoes. An alternative is that the first can be the first reflection from an object immersed in a fluid (the surface-water interface), and the second can be the second reflection (signal reflected from the back phase of the object).

According to the present invention, there are no frequency changes to cause phase shifts that would cause erroneous readings due to bonds, transducer plates, or electronic devices. Since the drive frequency remains fixed, all possible phase shifts, except those caused by changes in acoustic parameters, remain fixed. This means that the measuring system can monitor true changes in the acoustical system. Moreover, bond corrections and phase-adjust mechanisms make it possible to use the instrument of the present invention to determine the true phase velocity and its changes as a function of changes in thermodynamic parameters, with an enhanced sensitivity that one does not have with prior techniques.

Thus, the present invention combines the sensitivity of phase measurement with the inherent accuracy of constant frequency techniques, in a system that can be easily automated for measurements in ways that the echo-overlap systems cannot. Another advantage to the present invention is that the drive amplitudes associated therewith can be much lower than the pulse-superposition technique. This means that nonlinear effects such as might be encountered in the pulse-superposition method will not be a problem with the present invention. Additionally, the present invention will not be effected by frequency-dependent phase changes which have been associated with the Blume or Blume-related techniques.

The constant frequency pulsed phase-locked loop system of the present invention can be used to measure ultrasonic velocity or velocity changes in both liquids and solids.

For example, a travelling continuous sinusoidal plane wave propagating in the x-direction in a fluid has a wave motion given by the equation $$\Delta p = \Delta p_o \sin(kx - \omega t) \quad (1)$$

where $\Delta p$ is the excess pressure, $\Delta p_o$ is the amplitude of the excess pressure, k is the propagation constant, x is the distance, $\omega$ is the angular frequency, and t is the time. At a later time, $t + \Delta t$, so that the wave is described by $$\Delta p = \Delta p_o \sin(k(x + \Delta x) - \omega(t + \Delta t)) \quad (2)$$

The phase velocity of the wave is determined by considering the fact that the arguments in Eqs. (1) and (2) are equal. Hence, $$k(x + \Delta x) - \omega(t + \Delta t) = kx - \omega t, \quad (3)$$

and $$\Delta x/\Delta t = \omega/k = c, \quad (4)$$

where c is the speed of propagation of the wave. Using $$\omega = 2\pi f, \quad k = 2\pi/\lambda \quad (5)$$

where f is the frequency in hertz, and $\lambda$ is the wavelength, one can obtain from Eq. (4) the familiar expression $$f\lambda = c \quad (6)$$

It is to be noted that the phase of the argument of the sine wave, $(kx - \omega f)$, at a fixed t changes by $2\pi$ as the distance, x, is changed by $\lambda$. The phase shift, $\phi$, associated with a change in path length comes from periodicity condition expression, $$\phi/2\pi = \Delta x/\lambda \quad (7)$$

where $\Delta x$ is the change in path length.

Whenever phase comparision measurements are anticipated, one must select a phase reference point against which signals in the rest of the system can be referred. For example, the reference point may be chosen to be the synthesizer output, since it is at this point that all circuit signals originate, and hence are at the same phase. The signal propagates along two paths. The comparison of phase between these paths is made at the phase detector. The phase response of the acoustic system inserted in the first path is that which is to be measured. However, the phase detector responds to the difference in phase between the two paths.

There are many phase contributions in this measuring system. For the sake of simplicity constant circuit temperature can be assumed and the phase contributions can be grouped into three main areas: electronic (other than the phase detector), acoustic, and the phase detector. The electronic contributions, $\gamma_e$, come from electronic circuit phase differences between the two paths. The acoustic contributions come from the sample being measured, expressed by Eq. (7), the reflector contribution $\gamma_r$, and the transducer phase contribution $\gamma_t$. The phase detector contribution depends upon its design and its application. For the case treated here, the output stabilizes when the phase detector detects a quadrature $\gamma_q$ (nominally a contribution of $\pi/2$ or $3\pi/2$). It should be noted that except under certain conditions and for certain cases each of the phase terms possesses a frequency dependence. For example, the transducer has a complex electrical impedance $Z_t(f)$ but its phase contribution to $\gamma e$ is also altered by the cable configuration, frequency of operation, electrical impedances, and terminations. Solving Eq. (7) for $$\Phi = 2\pi\Delta x/\lambda + \gamma_r + \gamma_t + \gamma_e + \gamma_q \quad (8)$$

wherein $\Phi$ is the total phase shift of the system.

Substituting the total path traveled and combining all of the specific phase terms into a single total phase term $\gamma(f)$, which is a function of frequency, gives a total phase shift of $$\Phi = 4\pi l/\lambda + \gamma(f) \quad (9)$$

where l is the distance between the reflector and the transducer. Since the system operates in pulse-echo mode, $\Delta x = 2l$.

The measurements taken with the present invention make use of Eq. (9), since the system is sensitive to phase comparison between the received signal and the phase reference signal. The distance l is varied and the corresponding change in phase measured. Since the frequency is held constant, the wavelength and phase term $\gamma(f)$ is constant and $\Delta\Phi = \Delta\Phi$. Hence $$\Delta f = \lambda/4\pi\Delta\Phi \quad (10)$$

By plotting length change $\Delta l$ versus corresponding phase change $\Delta\phi$ one can experimentally determine the slope m and, consequently, the wavelength. With the synthesizer frequency f known to high accuracy we use Eq. (6) to determine the speed of sound which is given by $$c = 4\pi m f, \quad (11)$$

Figure 4:
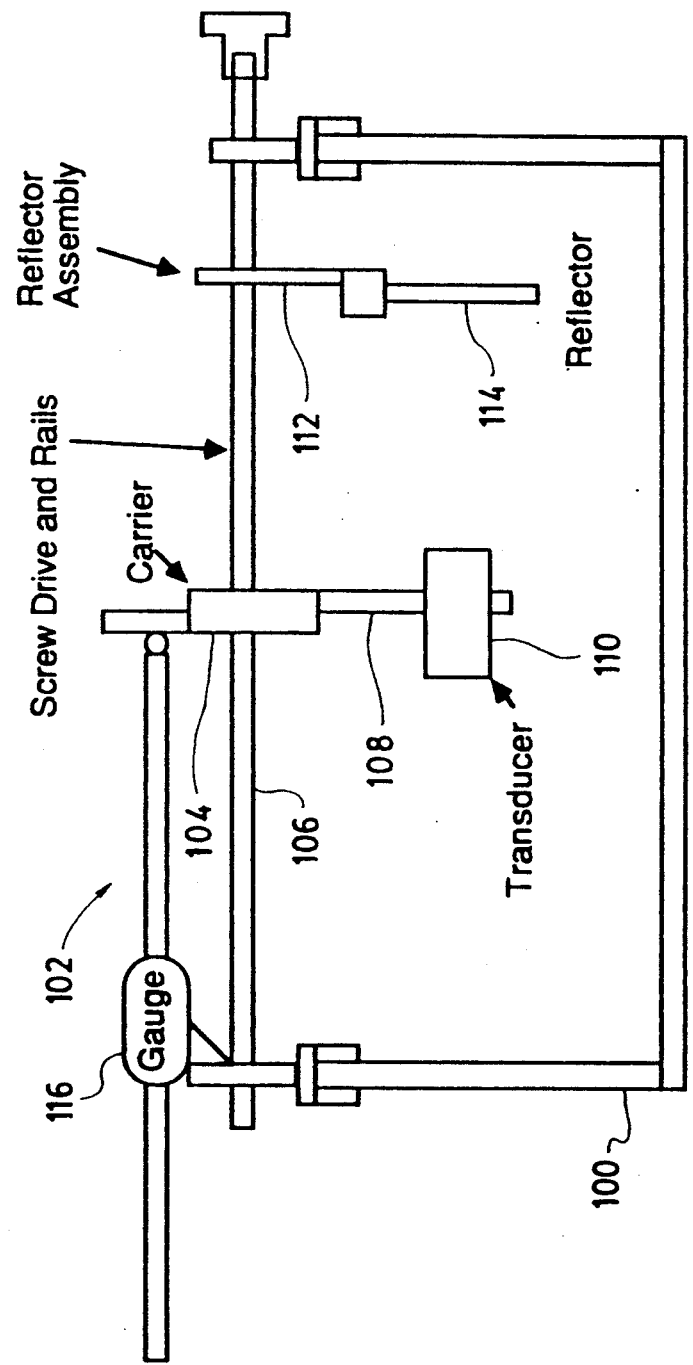
FIG. 4 is a schematic view of a test facility employing the present invention.

To demonstrate the present invention and referring to FIG. 4, a specially constructed tank 100 built from lucite was cleaned twice with a laboratory cleaning agent. It was rinsed with commercially prepared distilled water after each cleaning procedure and air dried. Specially prepared pure water (High Performance Liquid Chromatography Grade, Mallenckrodt ChromAR HPLC) was transferred to the tank. During the transfer process and throughout the measurements the tank and water were kept in an argon atmosphere.

A specially machined translation assembly 102 designed to fit on the tank and consisting of a carrier 104 attached to a system of two rails 106 and a screw drive is lowered into position and anchored to the top edge of the tank. Attached to the carrier is a transducer holder 108 constructed of stainless steel onto which a 5 MHz transducer 110 is attached. The transducer 110 is a compressional wave transducer made from a Lithium Niobate plate, 36° Y-cut, overtone polished and mounted in an air tight lucite holder to assure air backing.

A reflector holder 112 is suspended from the rails assembly onto which the reflectors 114 are attached and positioned as needed. The reflectors 114 are positioned as far from the transducer as the mounting equipment allows and aligned perpendicular to the propagation vector of the sound field.

Attached to the top of the carrier system is a dial gauge 116 with a range of 50 mm (Starrett 655-2081J) which is used to precisely determine the movement of the carrier relative to the end of the translation assembly. The dial gauge 116 has a total range of 50 mm with dial graduations of 10 $\mu$m. The scales are read with estimation to better than 3 $\mu$m for these measurements.

A precision thermometer (not shown), such as a Brooklyn Thermometer model 50 F., is used to record the temperature of the water before and after data collection. The temperature reported here is the average of the two measurements. The temperature variation is no more than ±0.01 C. The thermometer's accuracy is better than ±0.11 C.

Figure 5:
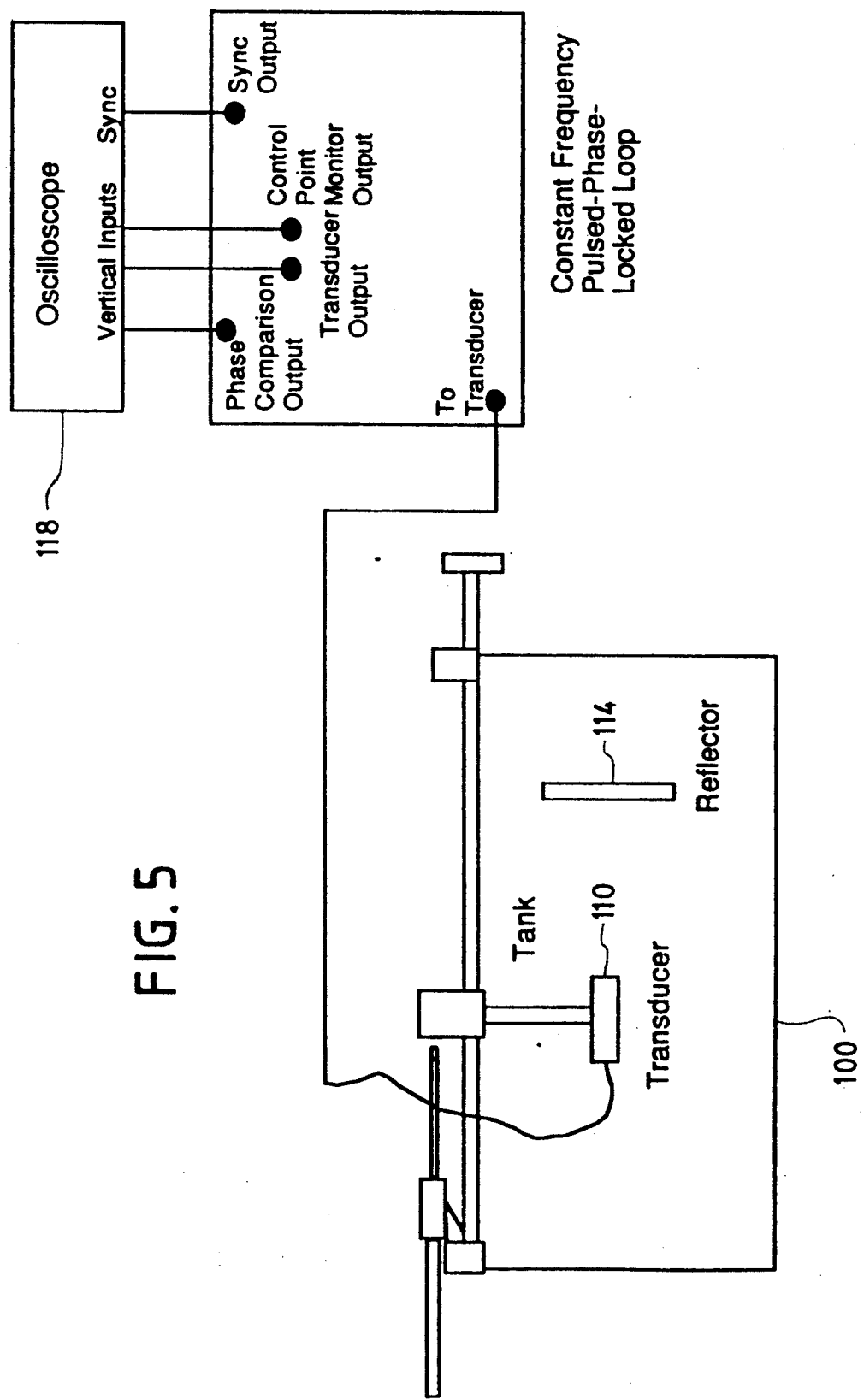
FIG. 5 is a schematic view of the test facility of FIG. 4, coupled to the constant frequency pulsed phase locked loop of the present invention.

FIG. 5 schematically shows the setup for the system used in these measurements. The oscilloscope 118 is adjusted to display the Transducer Output, the Phase Comparison Output, and the Control Point Monitor Output so that the timing pulses can properly be set for that portion of the phase signal to be measured. After alignment of transducer and reflector the phase of the first received echo is selected in all of these measurements. To assure that the phase value is stable a location well past midpoint of the echo toneburst phase display is chosen.

Data are taken by measuring and recording the phase changes and gauge reading changes as the carrier on the translation assembly is slowly advanced. For the phase measurements the Phase Shift Control Switch is set to the "Lock" position. The control voltage is measured with a voltmeter (Hewlett-Packard HP-3478A) and recorded.

Figure 6:
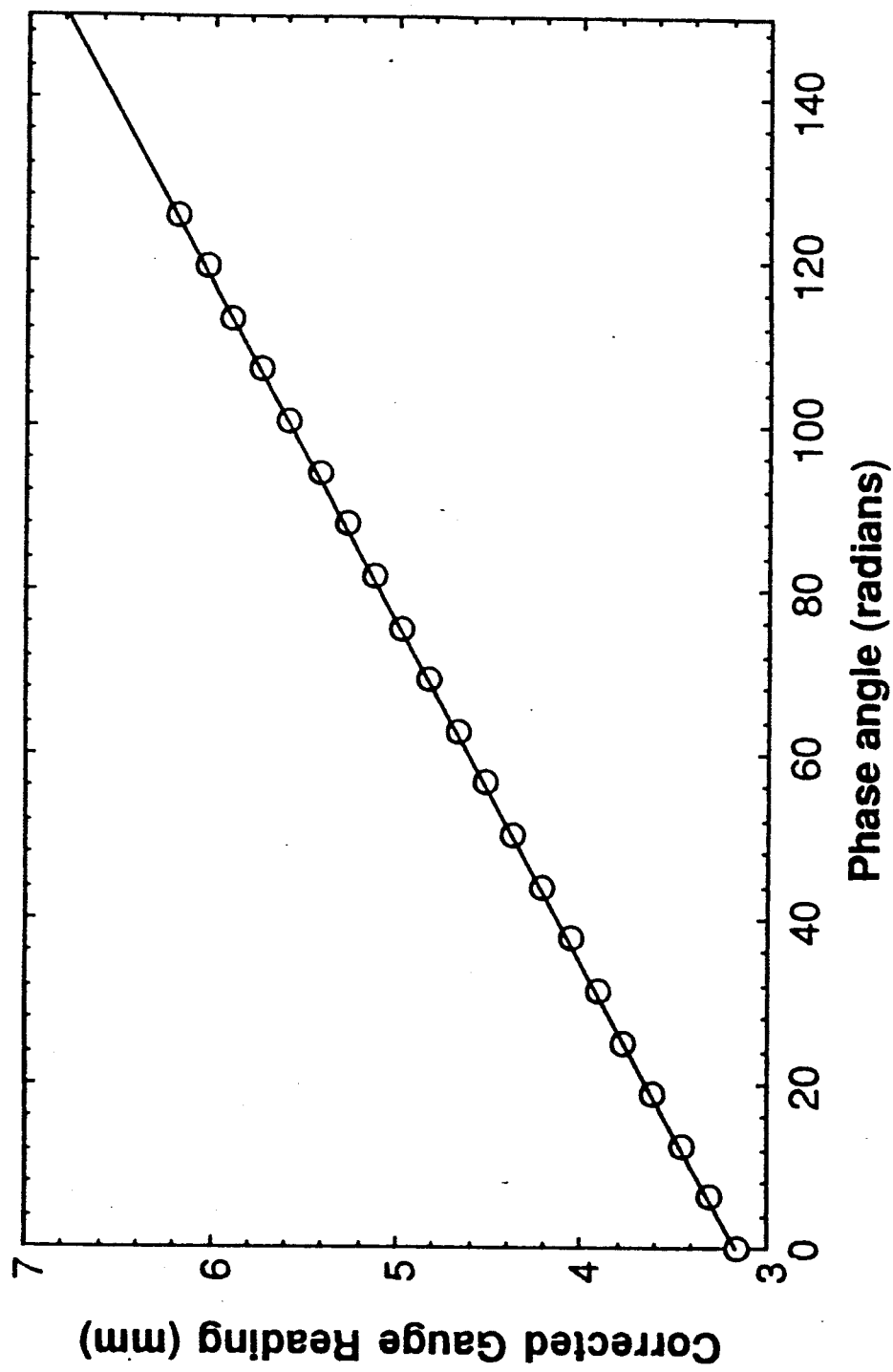
FIG. 6 is a graph showing measured phase angle.

The portion of the first echo chosen for phase comparison was well after reception of multiple reflections from the reflector. Under this condition the phase shift from the reflector depends on the thickness of the reflector. FIG. 6 shows a typical plot of the gauge reading versus phase change for these conditions. After correcting the gauge reading for a slight wobble in the translation apparatus a least squares fit of the data was used to calculate the slope.

Data for the above are given in Table 1 and include the reflector used, the operating frequency of the synthesizer, the water temperature, and the slope from the least squares fit of the data. The magnitude of the velocity is calculated using Eq. (11) (without diffraction correction) and given in the column labelled "Measured". Literature values for velocity of sound in water at temperatures 0, 10, 20, 30, and 40 C. were used for comparison with the present results. A three degree polynomial fit was used for the interpolated values taken from the literature and are presented in the column labelled "Calculated". The difference between the interpolated values and the measured values are listed in the columns labeled "Difference".

The value of the magnitude of the sound velocity in pure water as a function of temperature are in excellent agreement with the results quoted from the accepted values. Without application of diffraction corrections the agreement is within 0.18%. The uncertainty associated with the temperature measurement is estimated to contribute no more than ±55 cm/sec, while the uncertainty in length measurement is estimated to be no more than ±190 cm/sec. The reason for this large estimated uncertainty is due to the fact that the stage on the drive had some wobble. Uncertainties associated with phase measurements are insignificant in these calculations, but the system is estimated to be sensitive to better than parts in $10^7$. No attempt is made to account for any error associated with the interpolation fit employed with the literature values for velocity of sound in water at different temperatures. The velocity measured here in ultrapure water establishes that the present invention provides a reliable, accurate way to measure velocities, as well as for monitoring small changes in velocity without the sensitivity to frequency-dependent phase shifts common to other measurement systems.

TABLE 1

| Reflector | Operating Frequency (MHz) | Water Temp. (C.) | Slope ($10^{-2}$ mm) | Magnitude of Velocity ($10^{-5}$ cm/sec) Measured | Calculated | Difference |
|---|---|---|---|---|---|---|
| 1/4" glass plate | 5.0000 | 21.84 | 2.3646 | 1.4857 | 1.4883 | −.0026 |
| Glass slide | 4.7495 | 25.61 | 2.5153 | 1.5012 | 1.4988 | .0024 |

Numerous modifications and adaptations of the present invention will be apparent to those so skilled in the art and thus, it is intended by the following claims to cover all such modifications and adaptations which fall within the true spirit and scope of the invention.

What is claimed is:

1. A method of measuring phase shift in a sample, comprising:
   supplying a fixed frequency electrical output to a transducer coupled to the sample, thereby generating an acoustical tone burst in the sample which is received by the transducer which outputs a corresponding electrical echo signal; and
   measuring a counterbalancing phase shift required to bring about quadrature between the electrical echo signal and the fixed frequency electrical output.

2. A method according to claim 1, wherein the measuring includes comparing the phase of the fixed frequency electrical output and the electrical echo signal to provide an error voltage signal in accordance with a difference between the fixed frequency electrical output and the electrical echo signal, passing the error voltage signal to an integrator, adding a phase adjustment voltage to the integrator in an adder, and applying the added voltage to a phase shifter until a quadrature between the electrical echo signal and the fixed frequency electrical output is achieved.

3. An apparatus for measuring phase shifts in a sample, comprising:
   a logic and timing circuit;
   a buffer amplifier-phase shift circuit controlled by voltage;

a tone burst formation gate;

a fixed frequency oscillator coupled to and sending a constant frequency output to the logic and timing circuit as a clock signal, the buffer amplifier-phase shift circuit as a reference signal, and the tone burst formation gate;

a transducer coupled to the tone burst formation gate and being acoustically coupled to the sample, so that an electrical tone burst is sent to the transducer which generates an echo in the sample, the echo being received by the transducer which then generates an electrical signal which varies in accordance with the echo;

a mixer receiving and comparing phase of the echo generated electrical signal and the reference signal, and outputting an error signal voltage when the phase of the echo generated electrical signal and the reference signal are not in quadrature;

a sample and hold circuit receiving the error signal voltage and passing the error signal voltage to the phase shifter circuit through an integrator circuit; and means for adjusting the phase of the reference signal to match the phase of the echo signal.

4. An apparatus according to claim 3, wherein the adjusting means comprises an adder circuit receiving the voltage output of the integrator, and a phase adjustor having a variable voltage output received by the adder, the adder outputting an added voltage to the phase shift circuit to thereby adjust the phase of the reference signal.

5. An apparatus according to claim 4, further comprising a calibrated line stretcher through which the constant frequency output of the fixed frequency oscillator is delivered to the phase shift circuit, and being adjustable until the input voltage of the line stretcher matches the input voltage of the phase shift circuit.

6. An apparatus according to claim 5, wherein the phase shift circuit is calibrated by setting the phase shift circuit input voltage to zero volts.

7. An apparatus according to claim 6, wherein the phase shift circuit includes first and second phase shifters for comparing two different echo signals.

* * * * *